(12) United States Patent
Asp et al.

(10) Patent No.: US 6,468,409 B1
(45) Date of Patent: Oct. 22, 2002

(54) METHOD AND APPARATUS FOR DETECTING SUBSTANCES

(75) Inventors: Allan Asp, Uppsala; Bengt-Goran Andersson, Sollentuna, both of (SE)

(73) Assignee: Amersham Biosciences AB, Uppsala (SE)

( * ) Notice: Subject to any disclaimer, the term of this patent is extended or adjusted under 35 U.S.C. 154(b) by 0 days.

(21) Appl. No.: 09/254,758

(22) PCT Filed: Sep. 15, 1997

(86) PCT No.: PCT/SE97/01546

§ 371 (c)(1),
(2), (4) Date: Sep. 13, 2000

(87) PCT Pub. No.: WO98/11427

PCT Pub. Date: Mar. 19, 1998

(30) Foreign Application Priority Data

Sep. 16, 1996 (SE) ................................................ 9603344

(51) Int. Cl.⁷ ........................ G01N 27/26; G01N 21/64; G01N 21/76; G06K 9/00
(52) U.S. Cl. ........................ 204/461; 204/452; 204/603; 204/612; 382/128; 382/129; 436/172; 422/82.08
(58) Field of Search .................................. 382/128, 129; 204/452, 461, 603, 612; 356/344, 51; 436/172; 422/82.07, 82.08

(56) References Cited

U.S. PATENT DOCUMENTS

| | | | | |
|---|---|---|---|---|
| 3,822,097 A | * | 7/1974 | Allington | 256/435 |
| 5,062,942 A | * | 11/1991 | Kambara et al. | 204/612 |
| 5,290,419 A | * | 3/1994 | Kambara et al. | 204/612 |

* cited by examiner

Primary Examiner—Lyle A. Alexander
Assistant Examiner—Alex Noguerola
(74) Attorney, Agent, or Firm—Royal N. Ronning, Jr.; Stephen G. Ryan; Robert F. Chisholm

(57) ABSTRACT

An apparatus for detecting fluorophore labelled substances in an electrophoretic separation medium comprises illuminating means (1) for illuminating the fluorophore labelled substances (8), detecting means (7) for detecting fluorescence emitted by said fluorophore labelled substances upon illumination, and illumination varying means (9) for varying the illumination of the fluorophore labelled substances (8) to vary the intensity of the fluorescence.

7 Claims, 1 Drawing Sheet

METHOD AND APPARATUS FOR DETECTING SUBSTANCES

TECHNICAL FIELD

The invention relates to a method and an apparatus for detecting fluorophore labelled substances in an electrophoretic separation medium.

BACKGROUND OF THE INVENTION

When detecting fluorophore labelled substances in an electrophoretic separation medium, e.g. in connection with DNA sequencing, it is known that upon excitation, at some stage, the signal generated by a detector in response to the detected intensity of the fluorescence emitted by the substances, may fade out, e.g. due to the fact that there is too little fluorophore labelled DNA in the sample. There may also be other reasons for the signal to fade out.

It is also known that in some applications, e.g. fragment analysis, the opposite situation may arise, namely that the intensity of the fluorescence will be too high for the detector to handle, i.e. the detector will become saturated.

In both these cases, information about the separated substances may be lost. This can e.g. lead to that it will be impossible to determine the DNA sequence.

Proteins and carbohydrates are two other examples of substances that may be labelled with fluorophores and separated in an electrophoretic separation medium.

Patent abstracts of Japan, abstract of JP-A-7-151687, describes the prevention of reading errors of a basic sequence in a fluorescence detection type electrophoretic apparatus by monitoring the intensity of the excitation light. An alarm is generated when the detection signal from a photodetector is smaller than a predetermined reference value because of an abnormal intensity of the excitation light.

BRIEF DESCRIPTION OF THE INVENTION

The object of the invention is to eliminate the problems mentioned above.

This is attained by the method according to the invention by illuminating the fluorophore labelled substances, detecting fluorescence emitted by said fluorophore labelled substances upon illumination, and varying the illumination of the fluorophore labelled substances to vary the intensity of the fluorescence.

The above object is also attained by the apparatus according to the invention in that illuminating means are provided for illuminating the fluorophore labelled substances, detecting means are provided for detecting fluorescence emitted by said fluorophore labelled substances upon illumination, and illumination varying means are provided for varying the illumination of the fluorophore labelled substances to vary the intensity of the fluorescence.

BRIEF DESCRIPTION OF THE DRAWING

The invention will be described more in detail below with reference to the appended drawing on which the single figure, FIG. 1, schematically shows an embodiment of an apparatus according to the invention.

DESCRIPTION OF PREFERRED EMBODIMENTS

Figure 1:
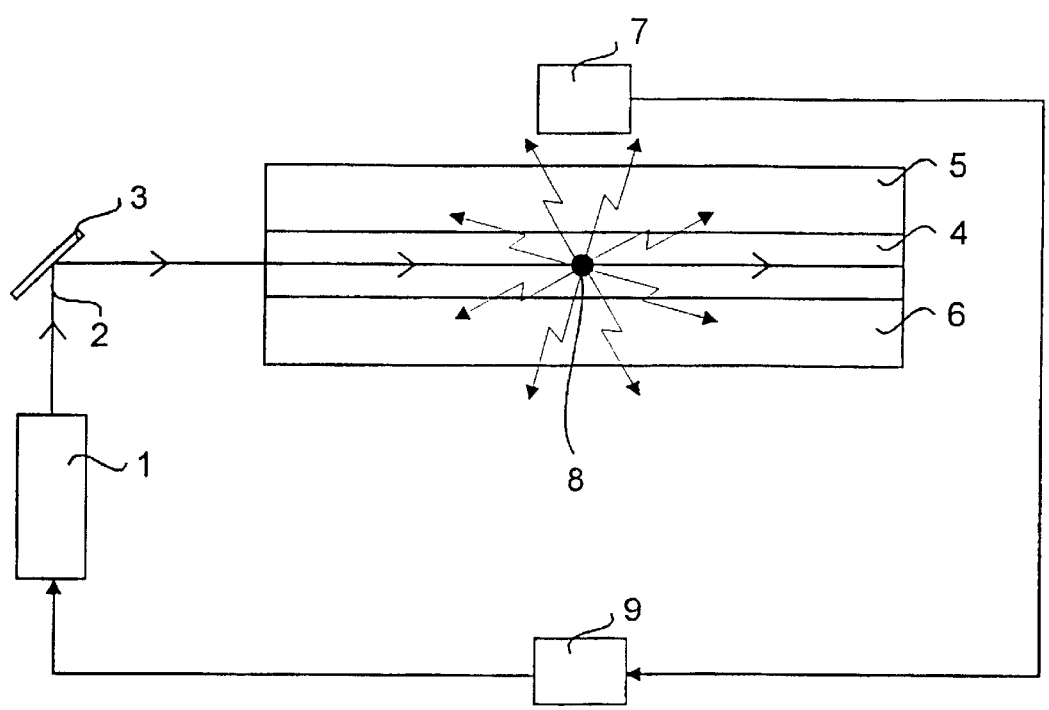

On the drawing, an embodiment of an apparatus according to the invention for detecting fluorophore labelled substances in an electrophoretic separation medium, is schematically illustrated.

The embodiment shown relates to a gel electrophoresis apparatus in which substances migrate in the separation medium, i.e. an electrophoresis gel.

However, it is to be understood that the invention is equally applicable to capillary electrophoresis.

Moreover, the invention may be applied not only to the above direct detection methods but also to indirect detection methods, i.e. methods where, first, the fluorophore labelled substances are separated in e.g. a gel, and where the gel, then, is placed in e.g. a laser scanner to detect e.g. the order of the substances.

On the drawing, 1 generally denotes a stationary illumination source. In the embodiment shown, the illumination source is supposed to be a laser diode which emits a laser beam 2. However, it is to be understood that a halogen lamp or any other suitable light source may be used as illumination source.

Via a mirror 3, the laser beam 2 is directed into an electrophoresis gel 4 through one of its lateral edges. In a manner well known per se, the gel 4 is provided between two glass plates 5 and 6.

The gel 4 is part of an electrophoretic separation system, not shown in any greater detail, for separating substances which are labelled with a fluorophore, and which under influence of an electric field migrate along migration lanes (not shown) in the gel 4.

When the fluorophore labelled substances migrating along the gel 4, pass through the laser beam 2, the fluorophore is excited to emit fluorescence. The fluorescence is detected by means of a photodetector 7 which is supported stationary in a manner not shown. The photodetector 7 is also adapted to generate a signal in response to the intensity of the detected fluorescence.

On the drawing, the excitation of a single fluorphore 8 in a single migration lane is schematically indicated, but it is to be understood that in a practical embodiment of the apparatus according to the invention, there are several, mutually parallel migration lanes in the gel 4 as well as a corresponding number of photodetectors 7.

The signal generated by the photodetector 7 in response to the intensity of the detected fluorescence, is then analyzed in order to determine e.g. a DNA sequence in a manner not illustrated.

In accordance with the invention, the signal generated by the photodetector 7 is also supplied to the input of an illumination varying circuit 9, whose output in the embodiment shown, is connected to the laser diode 1.

In a first embodiment of the invention, the illumination varying circuit 9 is adapted to compare the signal generated by the photodetector 7 with a reference value and, upon a predetermined deviation of the photodetector signal from that reference value, vary the power of the laser diode 1 in order to, hereby, vary the intensity of the fluorescence emitted by the fluorophore 8.

Thus, in case the signal from the photodetector 7 falls below a minimum reference value, the illumination varying circuit 9 is adapted to control the laser diode 1 to increase its output power to, thereby, increase the intensity of the fluorescence emitted by the fluorophore 8.

If, on the other hand, the signal from the photodetector 7 rises to a maximum reference value, e.g. to 90% of its dynamic range, the illumination varying circuit 9 is adapted to control the laser diode 1 to decrease its output power to, thereby, decrease the intensity of the fluorescence emitted by the fluorophore 8.

In a second embodiment of the invention, the illumination varying circuit 9 is adapted to sample the signal from the photodetector 7, and to compare successive samples. In dependence on that sample comparison, the illumination varying circuit 9 is adapted to control the laser diode 1 to either increase or decrease its output power.

If the comparison indicates that the intensity of the fluorescence has decreased a predetermined amount between two successive samples of the photodetector signal, the illumination varying circuit 9 is adapted to control the laser diode 1 to increase its output power to, thereby, increase the intensity of the fluorescence emitted by the fluorophore 8.

If, on the other hand, the comparison indicates that the intensity of the fluorescence has increased a predetermined amount between two successive samples of the photodetector signal, the illumination varying circuit 9 is adapted to control the laser diode 1 to decrease its output power to, thereby, decrease the intensity of the fluorescence emitted by the fluorophore 8.

In the latter embodiment, the output power of the laser diode 1 will be instantly varied when the deviation is detected so that the next sample of the photodetector signal will show either an increase or a decrease.

In accordance with the invention, instead of varying the power of the illumination source in response to the intensity of the detected fluorescence, the power of the illumination source may e.g. be constantly varied, e.g. modulated by a sinusoidal signal (not shown). In such a case, the instantaneous intensity of the detected fluorescence has to be correlated with the instantaneous power of the illumination source.

Also in accordance with the invention, an illumination source of constant power may be used. To vary the intensity of the fluorescence in such a case, e.g. a filter (not shown) having a variable transmittance may be placed between the illumination source and the electrophoretic separation medium. Instead of varying the power of the illumination source, the transmittance of the filter would, thus, be varied by the illumination varying circuit to vary the illumination of the fluorophore.

As should be apparent from the above, by varying the illumination of the fluorophore in accordance with the invention, the efficiency of the separation processes will be much improved.

The invention is, of course, not restricted to the embodiments specifically described above and shown in the drawing, but many variations and modifications may be made within the scope of the general inventive concept as defined in the following claims.

What is claimed is:

1. A method for detecting fluorophore labelled substances in an electrophoretic separation medium, comprising the steps of:
    illuminating the fluorophore labelled substances;
    detecting fluorescence emitted by said fluorophore labelled substances upon illumination by varying the illumination of the fluorophore labelled substances to vary the intensity of the fluorescence;
    generating a signal in response to the intensity of the detected fluorescence by increasing the illumination of the fluorophore labelled substances so as to increase the intensity of the fluorescence upon a fall of said signal below a minimum value, and decreasing the illumination of the fluorophore labelled substances so as to decrease the intensity of the fluorescence upon a rise of said signal above a maximum value.

2. A method according to claim 1, in which a signal is generated in response to the intensity of the detected fluorescence, chracterized by increasing the illumination of the fluorophore labelled substances to increase the intensity of the fluorescence upon a predetermined decrease in intensity between two successive samples of said signal, and decreasing the illumination of the fluorophore labelled substances to decrease the intensity of the fluorescence upon a predetermined increase in intensity between two successive samples of said signal.

3. A method according to claim 1, characterized in that the steps of illuminating the fluorophore labelled substances, and detecting the fluorescence emitted by said fluorophore labelled substances upon illumination, are carried out on fluorophore labelled substances migrating in an electrophoresis gel.

4. An apparatus for detecting fluorophore labelled substances in an electrophoretic separation medium, comprising:
    illuminating means for illuminating the fluorophore labelled substances; detecting means for detecting fluorescence emitted by said fluorophore labelled substances upon illumination;
    illumination varying means for varying the illumination of the fluorophore labelled substances to vary the intensity of the fluorescence;
    wherein said detecting means are adapted to generate a signal in response to the intensity of the detected fluorescence, and wherein said illumination varying means is adapted to increase the illumination to increase the intensity of the fluorescence upon a fall of said signal below a minimum value, and to decrease the illumination to decrease the intensity of the fluorescence upon a rise of said signal above a maximum value.

5. An apparatus according claim 4, in which the detecting means (7) are adapted to generate a signal in response to the intensity of the detected fluorescence, characterized in that said illumination varying means (9) is adapted to increase the illumination to increase the intensity of the fluorescence upon a predetermined decrease in intensity between two successive samples of said signal, and to decrease the illumination to decrease the intensity of the fluorescence upon a predetermined increase in intensity between two successive samples of said signal.

6. An apparatus according to claim 4, characterized in that said illumination varying means is adapted to constantly vary the illumination of the fluorophore labelled substances (8).

7. An apparatus according to claim 4, in which the detecting means are adapted to generate a signal in response to the intensity of the detected fluorescence characterized in that said illumination varying means comprises a filter of variable transmittance, which is placed between the illuminating means and the fluorophore labelled substances, and which is controlled by said signal to vary its transmittance.

\* \* \* \* \*